(12) United States Patent
Gofman et al.

(10) Patent No.: US 7,029,277 B2
(45) Date of Patent: Apr. 18, 2006

(54) CURING LIGHT WITH ENGINEERED SPECTRUM AND POWER COMPRESSOR GUIDE

(75) Inventors: Igor Y. Gofman, Croton-on-Hudson, NY (US); Joseph G. Colombo, Hackensack, NJ (US)

(73) Assignee: Coltene / Whaledent Inc., Cuyahoga Falls, OH (US)

( * ) Notice: Subject to any disclaimer, the term of this patent is extended or adjusted under 35 U.S.C. 154(b) by 241 days.

(21) Appl. No.: 10/273,394

(22) Filed: Oct. 17, 2002

(65) Prior Publication Data
US 2004/0076921 A1  Apr. 22, 2004

(51) Int. Cl.
*A61C 1/00* (2006.01)
(52) U.S. Cl. ...................................... 433/29
(58) Field of Classification Search ............... 433/29, 433/215, 216; 606/13, 14, 16, 17; 362/555, 362/119, 120, 800, 804, 231
See application file for complete search history.

(56) References Cited

U.S. PATENT DOCUMENTS

| | | | |
|---|---|---|---|
| 5,184,044 A | | 2/1993 | Thomas |
| 5,420,768 A | * | 5/1995 | Kennedy ................. 362/119 |
| 5,634,711 A | * | 6/1997 | Kennedy et al. ......... 362/119 |
| 6,331,111 B1 | | 12/2001 | Cao |
| 6,439,888 B1 | | 8/2002 | Boutoussov et al. |
| 6,554,463 B1 | * | 4/2003 | Hooker et al. ........... 362/555 |
| 6,638,063 B1 | * | 10/2003 | Otsuka .................... 433/29 |
| 6,692,250 B1 | * | 2/2004 | Decaudin et al. ......... 433/29 |
| 2001/0038992 A1 | | 11/2001 | Otsuka |
| 2002/0102513 A1 | | 8/2002 | Plank |
| 2003/0091955 A1 | * | 5/2003 | Burtscher et al. ......... 433/29 |

* cited by examiner

*Primary Examiner*—Todd E. Manahan
(74) *Attorney, Agent, or Firm*—Katten Muchin Rosenman LLP

(57) ABSTRACT

A light for a curing instrument includes a plurality of light sources, each producing an incident light beam. The incident light beams are combined to produce a single output beam, which exhibits a broader spectral width than any of the incident light beams. In one embodiment of the invention, the output beam exhibits an intensity over a spectral range defined by a first characteristic wavelength of a first of the plurality of light sources and a second characteristic wavelength of a second of the plurality of lights sources such that the intensity varies by no more than 25 percent over the range. In another embodiment of the invention including a one or more blue LED light sources among the plurality of light sources, at least one white LED is included in the plurality of light sources in order to generate an output light beam having a component portion that is characterized as green. In a third embodiment of the invention, a plurality of fiber optic bundles receive the incident light beams, and are arranged at a transmitting end so that individual fibers from the plurality of bundles are randomly combined to form a single output surface for transmitting the output beam.

7 Claims, 11 Drawing Sheets

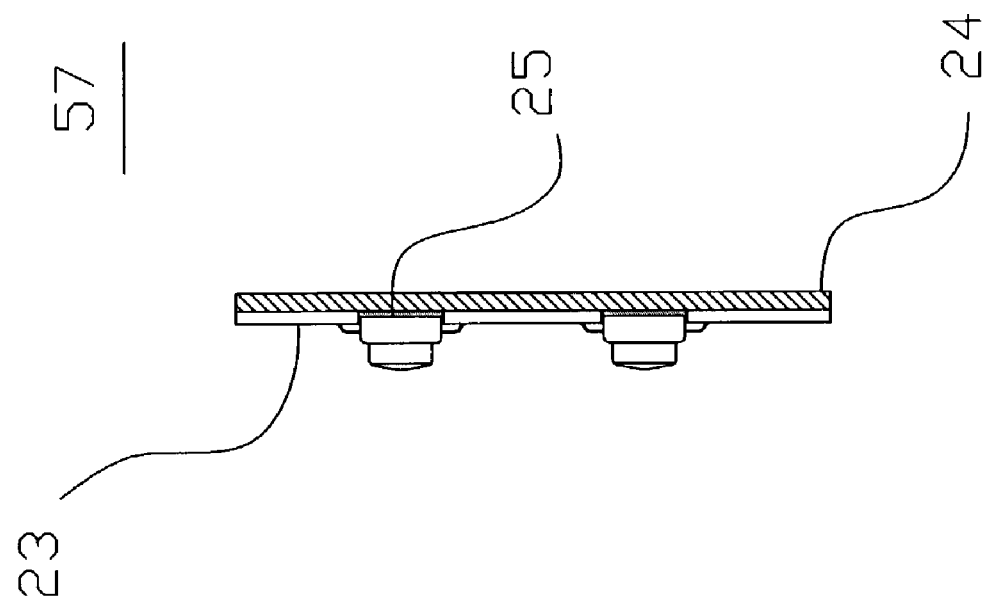
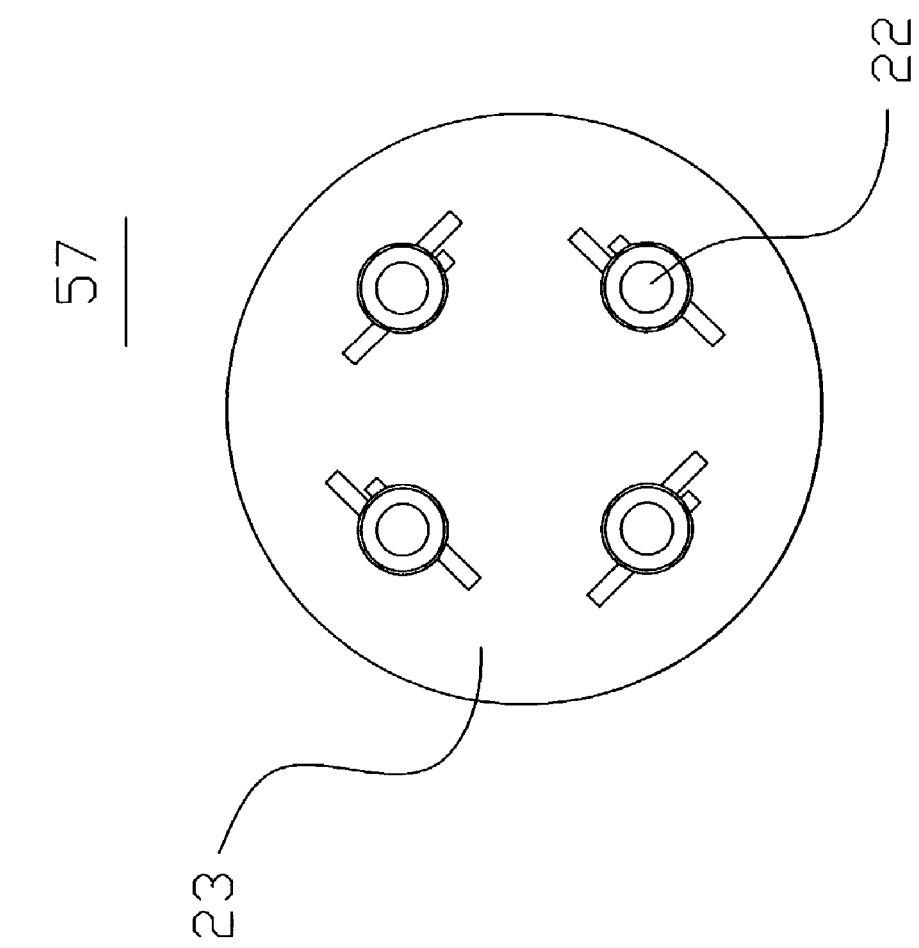

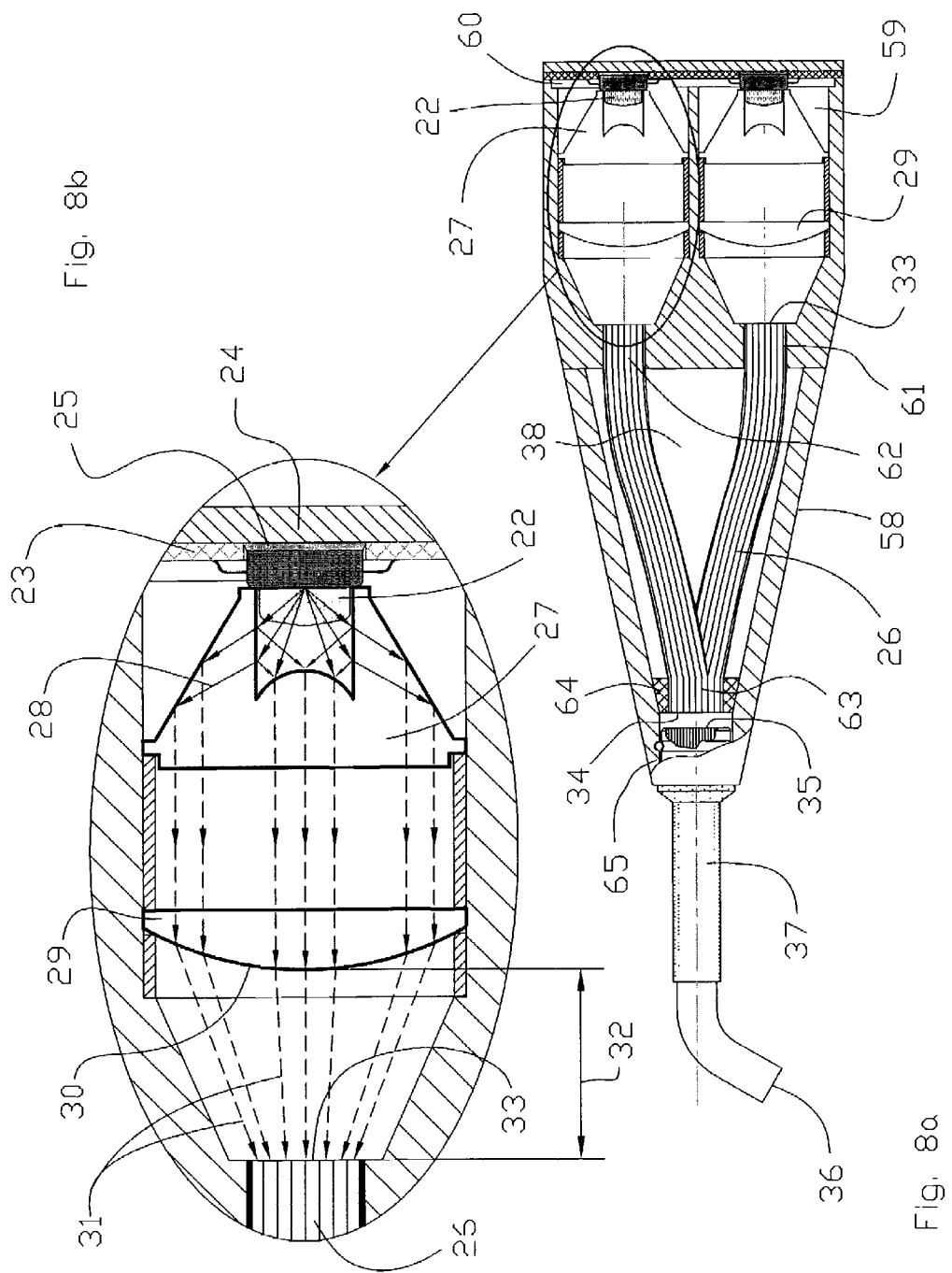

US 7,029,277 B2

CURING LIGHT WITH ENGINEERED SPECTRUM AND POWER COMPRESSOR GUIDE

FIELD OF THE INVENTION

The present invention relates to a light used for curing light-activated compound materials. In particular, the present invention relates to a curing light comprising two or more light sources whose outputs are integrally combined to produce a light spectrum suitable for curing a variety of light-activated compounds.

BACKGROUND OF THE INVENTION

Light-activated compounds are well known and used in a variety of commercial applications. For example, such compounds are widely used in a variety of dental procedures including restoration work and teeth filling after root canals and other procedures requiring drilling. Several well-known dental compounds have been sold, for example, under the trade names of BRILLIANT LINE, Z-100, TPH, CHARISMA and HERCULITE & BRODIGY.

Dental compounds typically comprise liquid and powder components mixed together to form a paste. Curing of the compound requires the liquid component to evaporate, causing the composite to harden. In the past, curing has been accomplished by air drying, which has had the disadvantage of requiring significant time. This time can greatly inconvenience the patient. More recently, use of composite materials containing light-activated accelerators has become popular in the field of dentistry as a means for decreasing curing times. According to this trend, curing lights have been developed for dental curing applications. An example of such a curing light is illustrated by U.S. Pat. No. 5,975,895, issued Nov. 2, 1999 to Sullivan, which is hereby incorporated by reference.

Conventional dental curing lights generally employ tungsten filament halogen lamps that incorporate a filament for generating light, a reflector for directing light and often a filter for limiting transmitted wavelengths. For example, a blue filter may be used to limit transmitted light to wavelengths in the region of 400 to 500 nanometers (nm). Light is typically directed from the filtered lamp to a light guide, which directs the light emanating from an application end of the guide to a position adjacent to the material to be cured.

Filters are generally selected in accordance with the light activation properties of selected composite compound materials. For example, blue light may be found to be effective to excite composite accelerators such as camphoroquinine, which has a blue light absorption peak of approximately 470 nanometers (nm). Once excited, the camphoroquinine accelerator in turn stimulates the production of free radicals in a tertiary amine component of the composite, causing polymerization and hardening.

An increasing number of light activated compounds are being developed using a variety of photo initiators with different light properties For example, orthodontic adhesives have been produced with a phenol propanedione accelerator that undergoes free radical production in the presence of green light having a light absorption peak of approximately 440 nm. In order to be effectively used with a variety of compounds, it would therefore be desirable to have a curing light capable of delivering light of several colors.

As halogen lamps typically produce a broad light spectrum, these lights would seem to provide some advantage over other more monochromatic light sources, such as light emitting diodes (LEDs) and laser diodes (LDs). However, a problem with conventional halogen-based lights is that the lamp, filter and reflector degrade over time. This degradation is particularly accelerated, for example, by the significant heat generated by the halogen lamp. For example, this heat may cause filters to blister and cause reflectors to discolor, leading to reductions in light output and curing effectiveness. While heat may be dissipated by adding a fan unit to the light, the fan may cause other undesired effects (for example, undesirably dispersing a bacterial aerosol that may have been applied by the dentist to the patient's mouth). Alternate lamp technologies using Xenon and laser light sources have been investigated, but these technologies have tended to be costly, consumed large amounts of power and generated significant heat. Laser technologies have also required stringent safety precautions.

LEDs and LDs appear to be good alternates to halogen curing light sources, having excellent cost and life characteristics. Generating little heat, they also present less risk of irritation or discomfort to the patient. However, LEDs and LDs individually tend to produce relatively monochromatic light energy.

U.S. Pat. No. 6,331,111 to Cao discloses a curing light system incorporating a plurality of LEDs or LDs in a single curing light. The plurality of LEDs or LDs are located on a single heat sink to facilitate heat dissipation, and radiate light through a transparent focus dome or window toward a curing target. Cao notes that LEDs and LDs may be selected having different characteristic wavelengths in order to cure a variety of composite materials having photo initiators sensitive to these different characteristic wavelengths. However, Cao falls short of disclosing an efficient means for combining light energy from monochromatic light sources of a few colors in order to produce a broad, continuous spectrum of light energy for curing a variety of composite materials.

SUMMARY OF THE INVENTION

Limitations of the prior art are overcome by a novel curing light comprising a plurality of light sources each producing an incident light beam, and means for integrating the plurality of incident light beams into a single output light beam. In a first embodiment of the present invention, at least a first one of the light sources has a first characteristic wavelength and at least a second one of the light sources has a second characteristic wavelength, selected so that the output light beam exhibits an intensity that varies by no more than 25 percent over a range defined by the first and second characteristic wavelengths. This result may be achieved, for example, where the first one of the light sources has a first spectral width ending at an uppermost wavelength and the second one of the light sources has a second spectral width ending at a lowermost wavelength, by selecting the first and second light so that the uppermost wavelength of the first light source and the lowermost wavelength of the second light source are approximately coincident.

In a second embodiment of the present invention, where at least one of the at least one of the light sources is a light emitting diode (LED) that produces an incident light beam characterized as blue, another light source is selected to be an LED that produces an incident light beam characterized as white, so that the output light beam contains a light component that is characterized as green.

In a third embodiment of the present invention, the means for integrating the incident light beams comprises a plurality of fiber optic bundles, wherein a receiving end of each fiber optic bundle is arranged to receive an incident light beam from one of the plurality of light sources, and transmitting ends of fibers in each of the plurality of fiber optic bundles are randomly combined to form a single output surface for transmitting the output beam.

BRIEF DESCRIPTION OF THE DRAWINGS

A more complete understanding of the invention may be obtained by reading the following description of specific illustrative embodiments of the invention in conjunction with the appended drawing in which:

FIGS. 6a, 6b, 8a, 8b and 9 illustrate apparatus embodying principles of the present invention.

In the various figures, like reference numerals wherever possible designate like or similar elements of the invention.

DETAILED DESCRIPTION OF THE PREFERRED EMBODIMENTS

The following detailed description includes a description of the best mode or modes of the invention presently contemplated. Such description is not intended to be understood in a limiting sense, but to be an example of the invention presented solely for illustration thereof, and by reference to which in connection with the following description and the accompanying drawing one skilled in the art may be advised of the advantages and construction of the invention.

Figure 1:
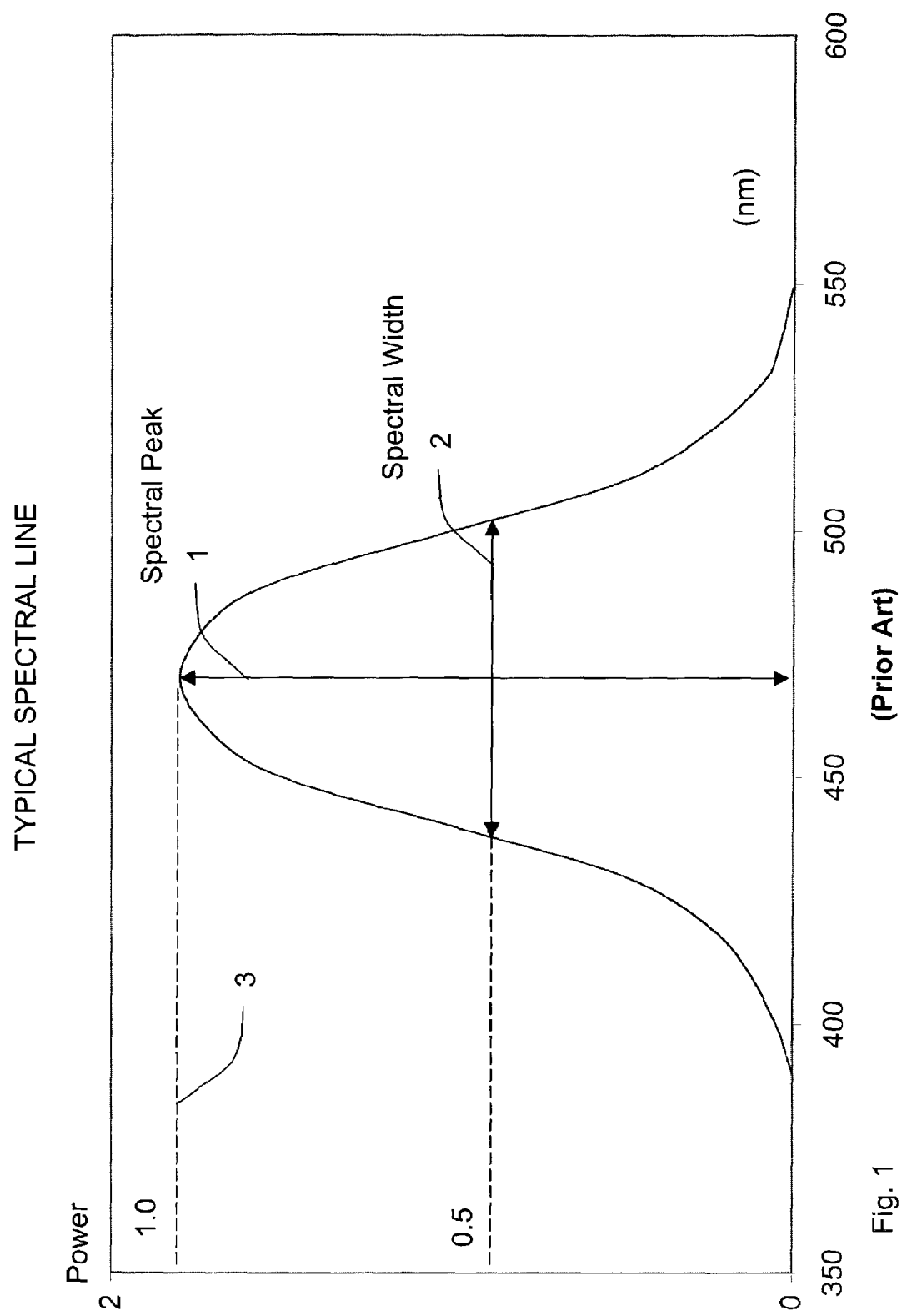
FIG. 1 shows a typical spectral line for a conventional light source.

FIG. 1 illustrates a typical spectral line for a light source. Light energy concentrates near a peak (central) wavelength 1 ($\lambda_p$,), where a relative light power reaches a maximum relative value 3 of 1.0 at the peak wavelength 1. Here, power may be measured, for example, as an electrical output from a photodetector that is indicative of the light intensity.

The further a wavelength deviates from the peak wavelength, $\lambda_p$, the lower its light power amplitude. An important characteristic of this spectral line is its spectral width 2 ($\Delta\lambda$), which is conveniently defined to be the width in nanometers (nm) of the spectral line between wavelengths producing a power that is half of maximum relative power value 3. With increased spectral width, more colors are effectively emitted by the light source. As previously suggested, an unfiltered halogen light may effectively transmit light over a bandwidth (spectral width) of 100 nm. By way of contrast, an LED's spectral width may be on the order of tens of nm, while a LD's typical width may be 1 nm or less.

Figure 2:
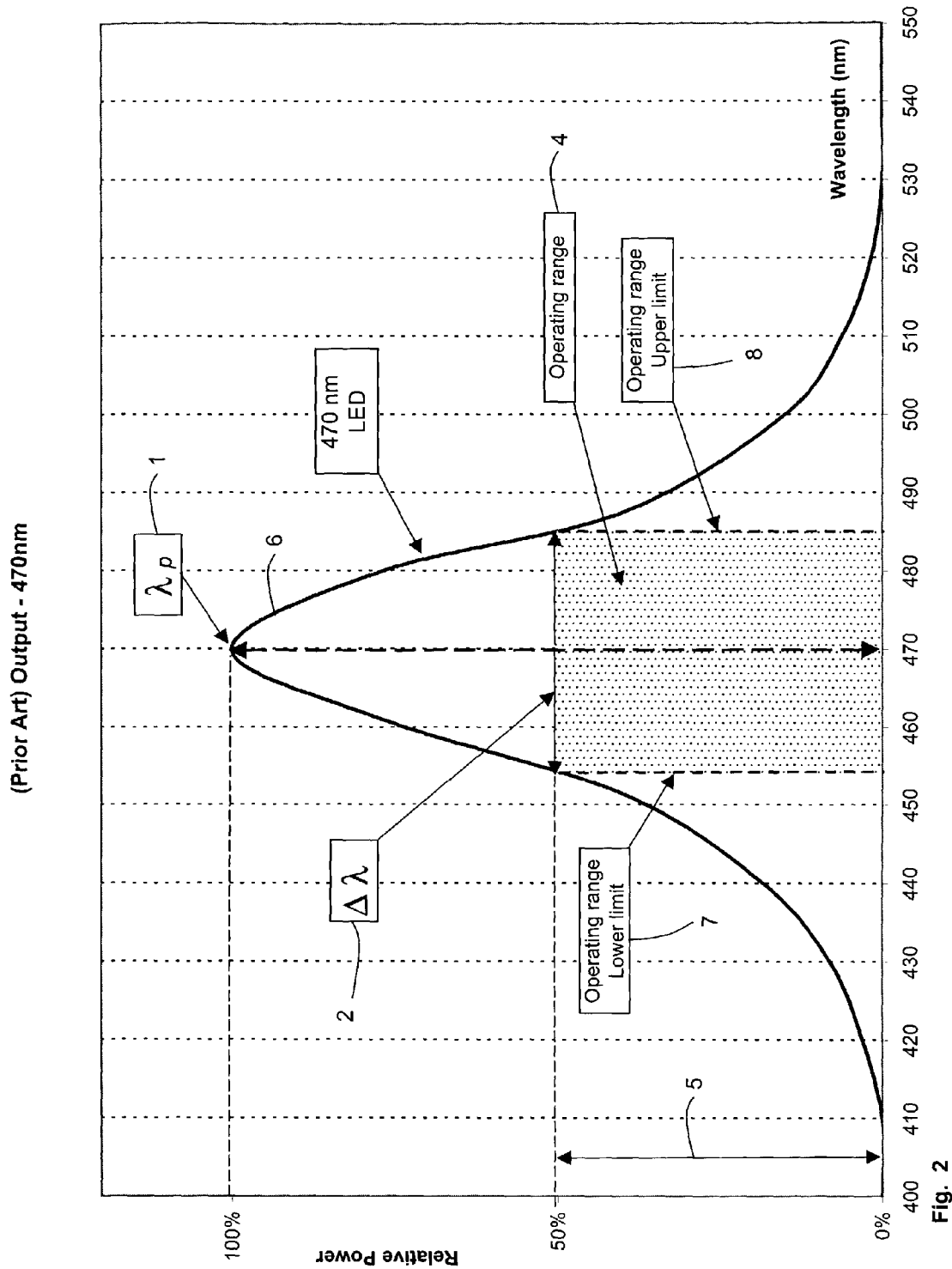
FIG. 2 shows a typical spectral line for a conventional light emitting diode (LED)

FIG. 2 illustrates a spectral line 6 for a typical LED having a central wavelength 1 of 470 nm. An operating range 4 is defined by the spectral width 2, and is shown in FIG. 2 as a grayed region under spectral line 6 with boundaries at lower limit wavelength 7 and upper limit wavelength 8. Within this range, light power is produced at a minimum level 5 no less that 50 percent of the maximum power produced at central wavelength 1.

Composite compound material manufacturers typically quote standard cure times for a light source operating at a minimum of 50 percent of a maximum power output level. As a result, outside of operating range 4, the relative power of the LED it typically too low to polymerize a composite material within the standard cure times quoted by a material's manufacturer. Conversely, any composite material having a light activated component sensitive to a wavelength within operating range 4 can generally be cured by the light source within the manufacturer's quoted times.

LEDs are often considered to produce light that is effectively monochromatic, or consisting of one color. As illustrated by FIG. 2, even the monochromatic light of an LED is however composed of a range of wavelengths. Visible light ("white light") ranges approximately from 400 nm to 700 nm (in other words, white light has a spectral width of about 300 nm). An LED typically appears to produce one color because the spectral width of an LED's visible radiation is relatively narrow at approximately 30 nm. As spectral width narrows, light appears to be increasingly monochromatic.

Light-activated composite materials are used in a variety of commercial applications. For example, light-activated composite materials are widely used as adhesives (for example, in the semiconductor industry) and as fillers (for example, in the dental industry). Dental resins are very well known in the dental industry for the restoration of primary teeth. They are available in a variety of shades, and typically polymerize with a dental curing lamp producing visible light in a range between 400 to 500 nm. Within this range, manufacturers may produce as many as 10 to 15 different shades of composite resins for various applications, each activated by light emanating at a different wavelength in the visible range. As a result, no single LED light source is effective to activate each of these composite resins.

Figure 3:
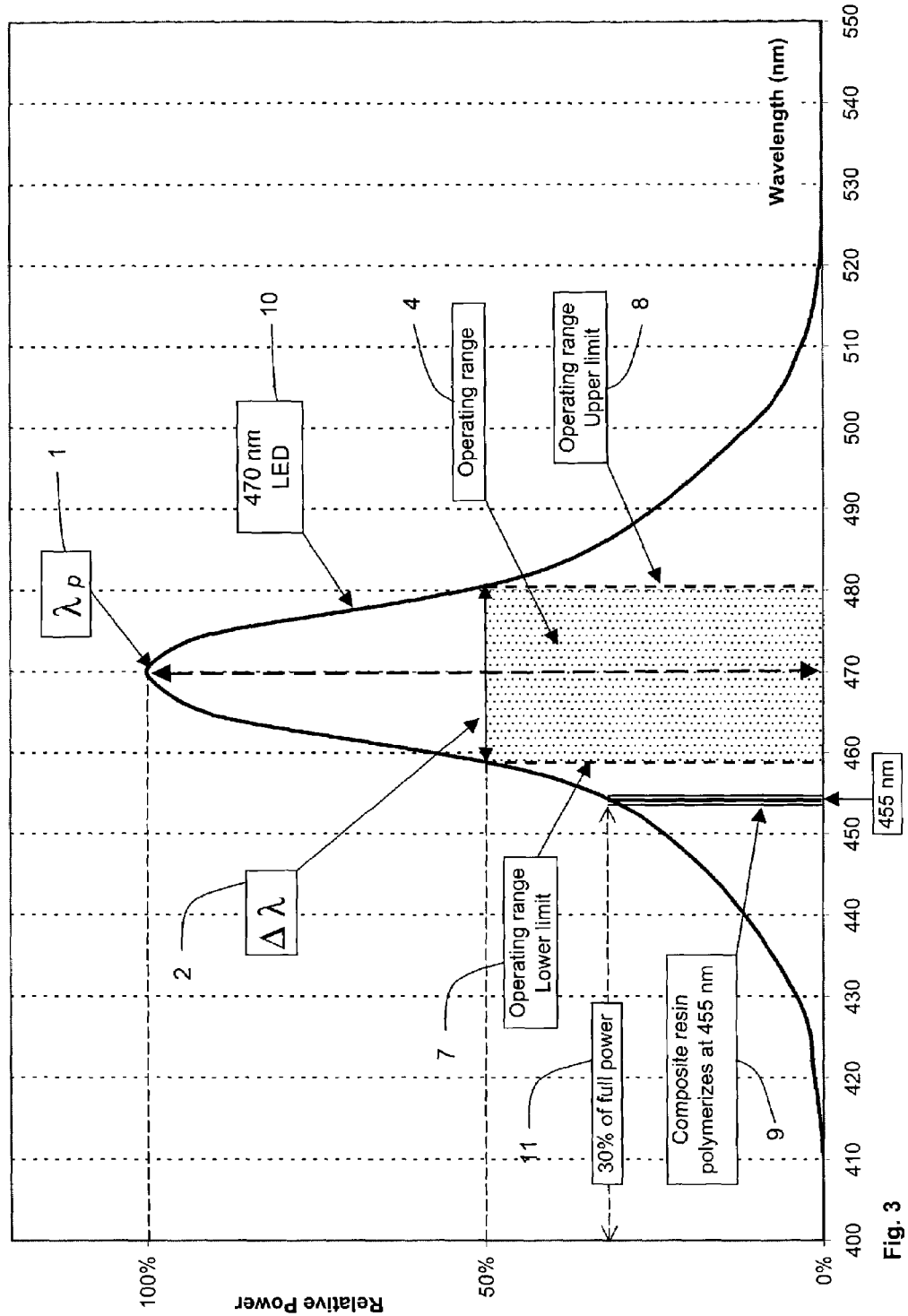
FIGS. 3, 4 illustrate the effects of using an LED light to cure a composite resin, when the composite resin includes an accelerator activated by light energy at a wavelength outside of the spectral width region of the LED.

FIG. 3 shows the spectral line 6 of FIG. 2 with relation to a composite resin having a polymerizing wavelength 9 of 455 nm. As shown in FIG. 3, polymerizing wavelength 9 lies outside of the spectral width 2 of LED 10 having a central wavelength 1 of 470 nm. Thus, a curing light based on LED 10 would be ineffective for curing the resin activated at wavelength 9. Note that LED 10 produces a diminished power level 11 representing only 30% of its maximum light intensity at wavelength 9.

Figure 4:
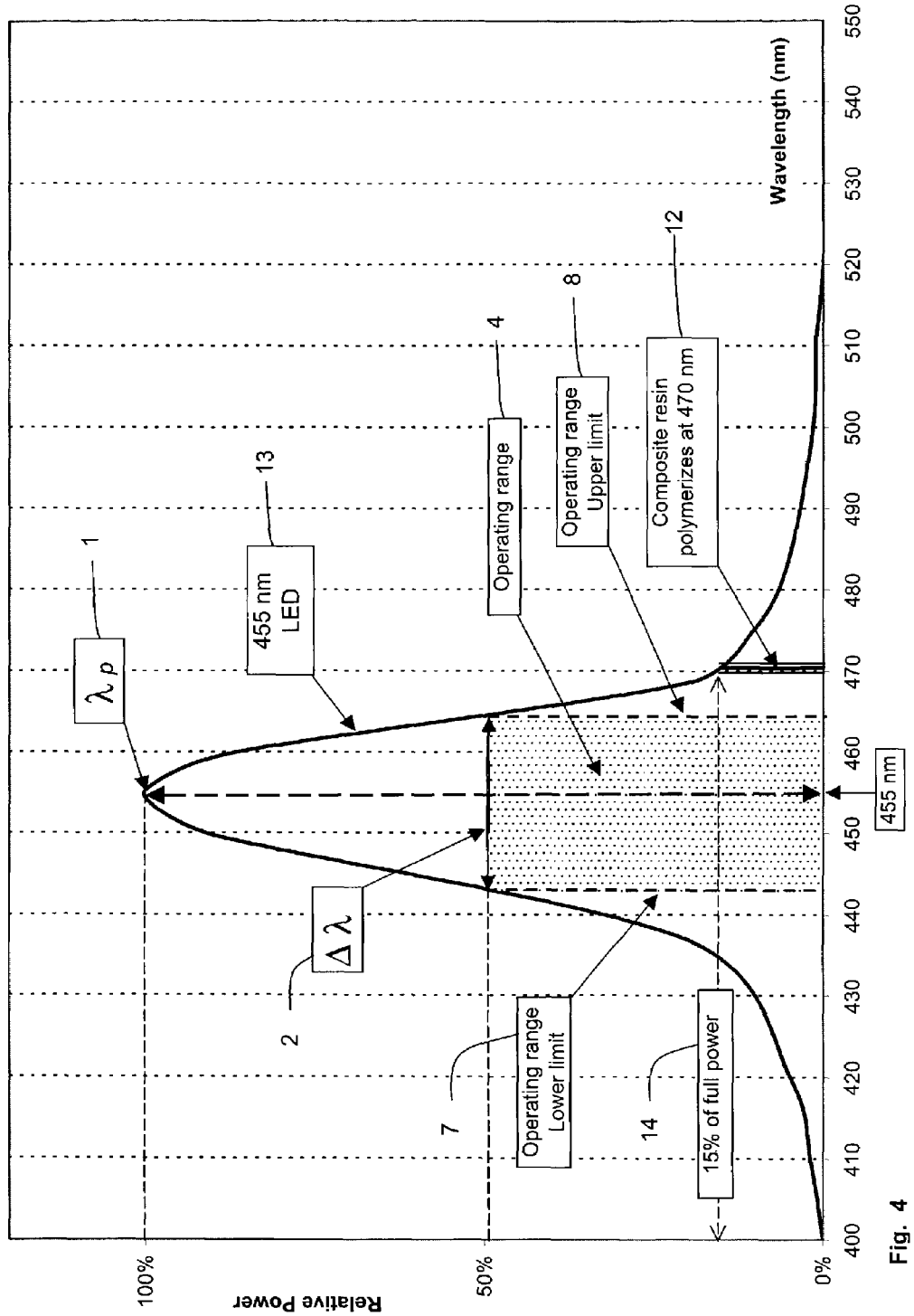

As shown in FIG. 4, alternately, for a composite resin that polymerizes at wavelength 12 of 470 nm, wavelength 12 would lie outside of the spectral width 2 of LED 13 having a central wavelength 1 of 455 nm. In this case, LED 13 produces a diminished power level 14 representing only 15% of its maximum light intensity at wavelength 12.

By way of contrast, the present invention operates to integrate light supplied by several carefully-selected monchromatic light sources in order, for example, to produce light having a spectral width encompassing wavelengths for the more popular light-activated dental compounds. The development of this "engineered" light spectrum will now be explained with reference to FIGS. 5, 7 and 7a.

Figure 5:
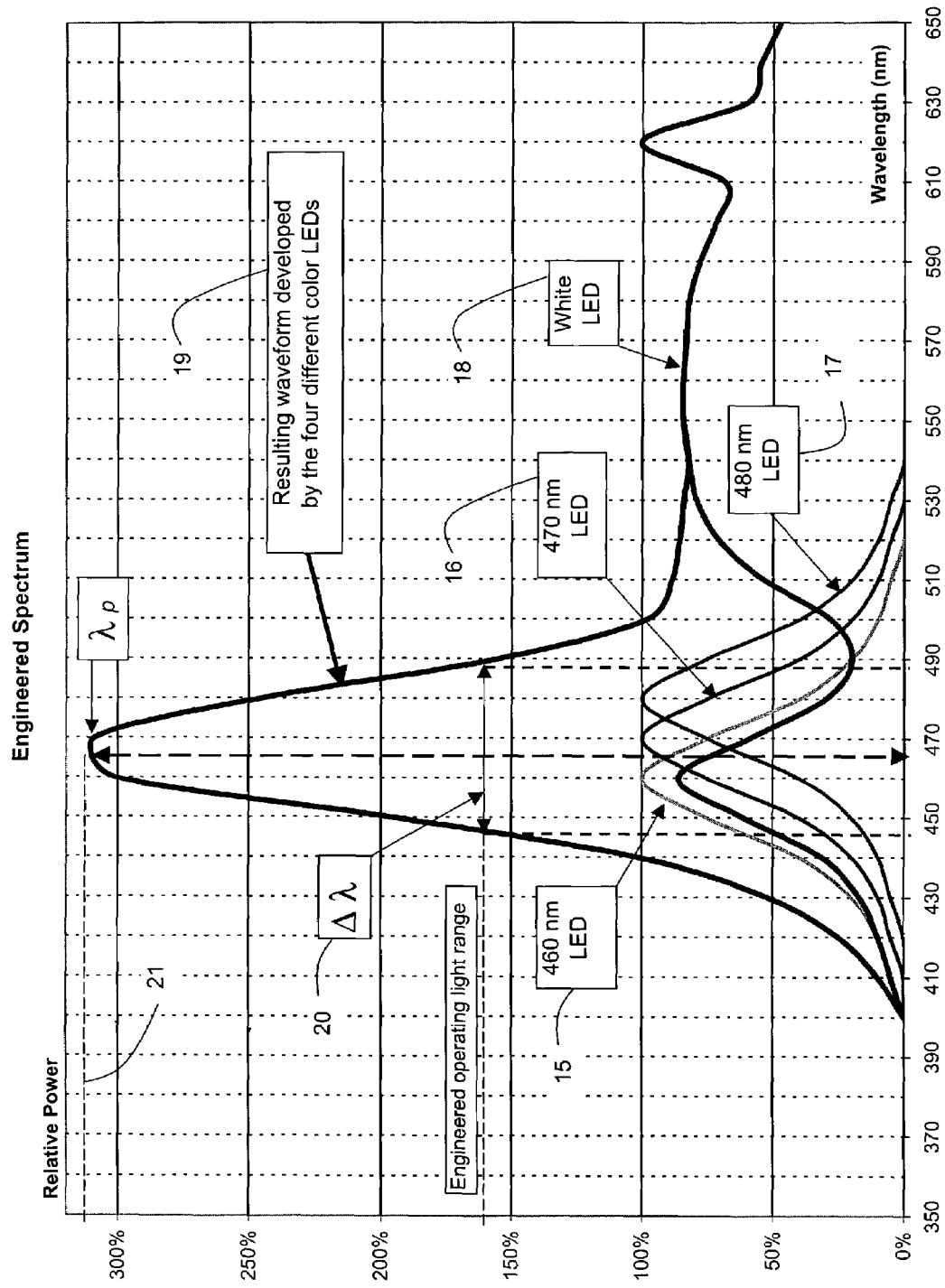
FIGS. 5, 7 and 7a illustrate principles and embodiments of the present invention relating to an engineered light spectrum.

FIG. 5 provides a composite graph illustrating principles of the present invention. In FIG. 5, spectral performance characteristics are illustrated for an engineered light source comprising combined outputs from 4 LED light sources. Accordingly, FIG. 5 shows spectral lines for a "Royal Blue" LED 15 centered at 460 nm (for example, Nichia Corporation part number NSPB500SV), a "Blue" LED 16 centered at 470 nm (for example, Nichia Corporation part number NSPB500SW470), and an "Aqua Blue" LED 17 centered at 480 nm (for example, Nichia Corporation part number NSPB500SX), and a "White" LED 18 (for example, Nichia Corporation part number NSPW500BS). LED 18 is introduced for the following reason. There are a small percentage of accelerators used in dental composites that do not chemically react with visible blue light wavelengths. Through a number of experiments, we determined that a splash of white light added to a blue light source is effective to stimulate such accelerators, in particular those that require a splash of green spectral light. One skilled in the art will readily recognize that white LED 18 may also be added with a similar effect to other groups of LEDs selected to produce one of the other visible colors (for example, red, orange, yellow, indigo and violet). For example, three "red" LEDs could be selected to produce each producing outputs centered at one of 625 nm, 660 nm and 700 nm. This and all other such single color/white light source combinations are fully contemplated by the present invention.

As shown in FIG. 5, light output from LEDs 15–18 may be combined to produce spectral line 19, which exhibits a spectral width 20 that is much broader than the spectral widths of the individual LEDs 15–18. In addition, the maximum relative power 21 for the combined spectral line 19 is substantially higher than the maximum relative power individually produced by each of the four LEDs 15–18 (shown in FIG. 5 each at a reference level of 100 perecent). In the example of FIG. 5, the maximum relative power 21 of spectral line 19 is about 3 times higher than the reference level.

Figure 7:
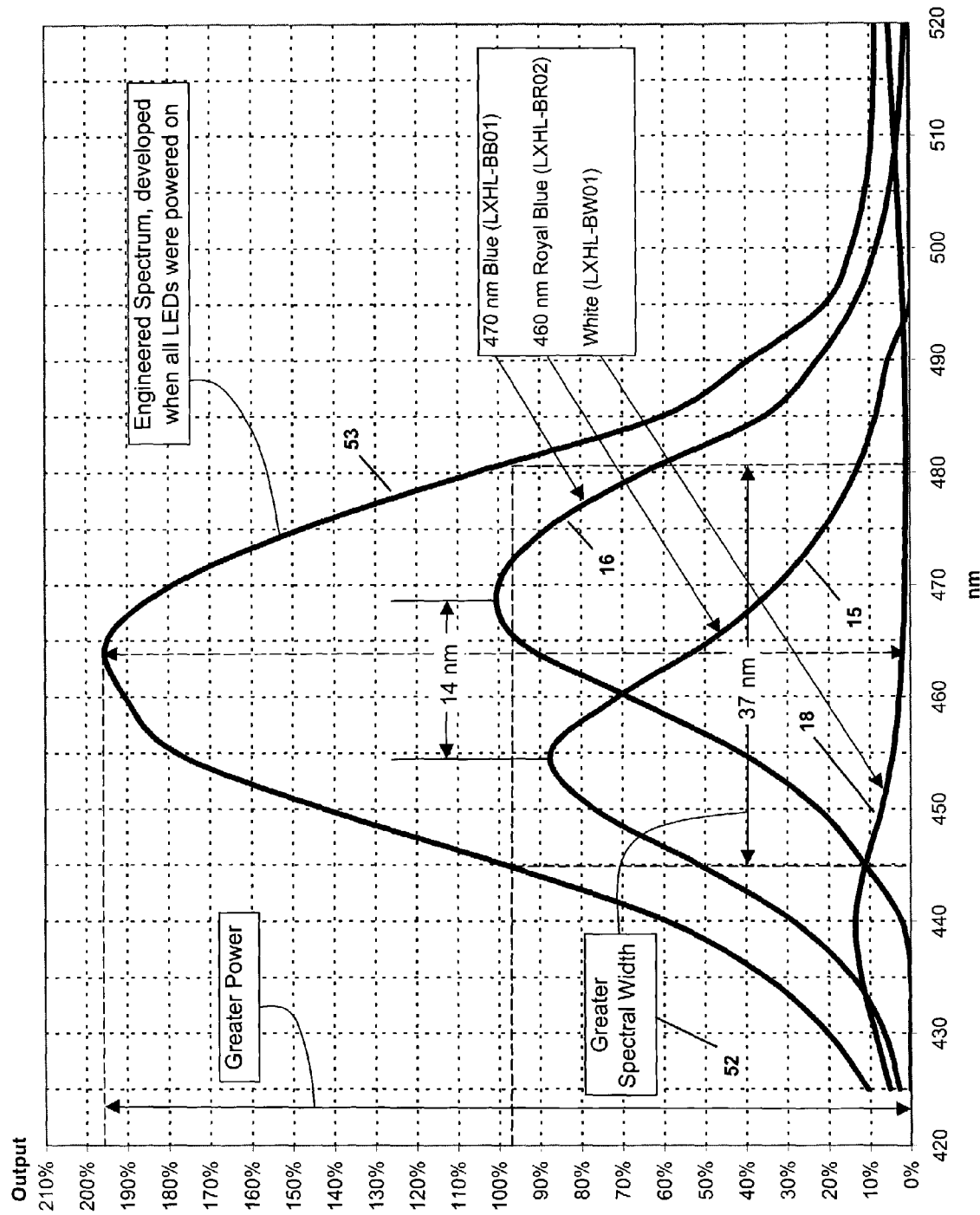
Figure 7A:
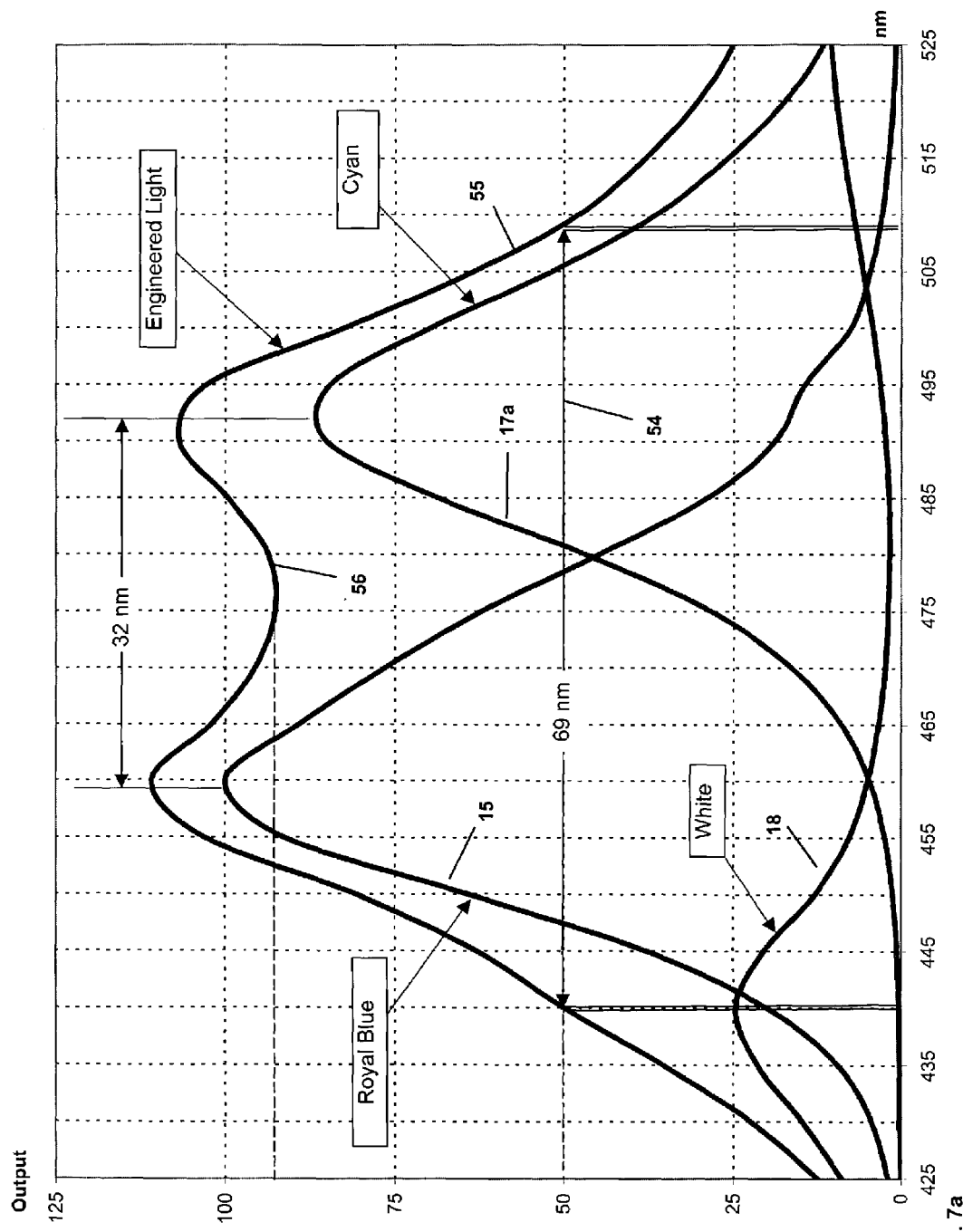

FIG. 7 illustrates the spectral performance of an embodiment of an inventive engineered light source comprising a 470 nm "Blue" LED 16 (Luxeon part number LXHL-BB0I Blue), a 460 nm "Royal Blue" LED 15 (Luxeon part number LXHL-BR02), and a "White" LED 18 (Luxeon part number LXHL-BW0I). FIG. 7a illustrates the spectral performance of an alternate light source to the light source of FIG. 7, replacing the 470 nm "Blue" LED 16 of FIG. 7 with a 505 nm "Cyan" LED 17a (Luxeon part number LXHL-BE01).

In the engineered light source of FIG. 7, the center spectral wavelengths for the blue LEDs 15, 16 are positioned approximately 14 nm apart, producing a spectral width 52 as shown in the spectral line 53 for the combined light source of 37 nm. Spectral line 53 over spectral width 52 exhibits a relative power that is nearly at or above the maximum power levels of the individual LEDs over this range. With the selected LEDs 15, 16 and 18, for example, a maximum power output of approximately 1200 milliwatts per centimeter square (mw/cm$^2$) output may be achieved by the emgineered light source of FIG. 7.

In FIG. 7a, the center spectral wavelengths for LEDs 15, 17a are more widely separated at approximately 32 nm apart, producing a spectral width 54 as shown in the spectral line 55 for the combined light source of 69 nm. While relative power drops to a diminished level 56 near the center of the spectral width 54 due to the increased separation, even at its lowest level, relative power remains nearly at the maximum relative power levels shown for individual LEDs 15, 17a.

In the example of FIG. 7, output power can be substantially increased by replacing the LED 16 with a more powerful 470 nm LED (Luxeon part number LXHL-LB5C), replacing LED 15 with a more powerful 460 nm LED (Luxeon part number LXHL-LR5C), and replacing LED 18 with a more powerful white LED (Luxeon part number LXHL-LW5C), or their equivalent. This combination produces a combined power output in excess of 4000 mw/cm$^2$.

FIGS. 6 and 8–10 illustrate novel apparatus embodying principles of the present invention. FIGS. 8a,b show an embodiment of the present invention employing a fiber optic cable assembly 26 that receives light produced by individual LEDs 22 at input surfaces 33, and conducts light to a transmitting surface 34, to be re-directed to input surface 35 of fiber optic light guide 37. Light is directed by conventional light guide 37 to transmitting surface 36 for application, for example, to polymerize a dental composite resin. Assembly 26 may be preferably constructed with optical fibers having a numerical aperture (NA) of approximately 0.66, and arranged such that individual fibers directed from input surfaces 33 are randomly ordered within the area defined by transmitting surface 34.

FIGS. 6a and 6b illustrate aspects of a carrier 57 for physically packaging the LEDs 22. By way of example, carrier 57 comprises four surface mount LEDs 22 (available, as described above, as LUMILED LEDs from Luxeon), a printed circuit board 23, a heat sink 24 for dissipating heat away from the base of the LEDs 22, and thermal conductive compound 25 to assist in the transfer of heat from the base of each LED 22 to the surface of the heat sink 24.

As shown in FIGS. 8a, b, circuit board 23 and heat sink 24 of carrier 57 of FIGS. 6a, 6b are fixedly positioned abutting a lip surrounding rearward recess 60 in a light housing 58. Each LED 22 is further fitted to a collimator lens 27 (for example, Luxeon part number LXHL-NXO5) for directing light rays 28 received from LED 22 toward an input surface 33. Such collimator lenses are known to have light transmission efficiencies of up to 90%, and to deliver a concentrated light beam of about 10 mm in diameter, with some minor losses due to stray output beams.

To improve upon the effectiveness of collimator lens 27, the present invention also comprises planar-convex, anti-reflective lens 29 for further focusing and concentrating light rays produced by lens 27 towards input surface 33 (illustrated in FIG. 8a as light rays 31). A suitable lens may be found, for example, as Edmund Industrial Optics part number L45-238, selected to have a diameter approximately equal to a maximum diameter of collimator lens 27. An output curvature (thickness) 30 of the lens 29 may be selected for directing light beams 31 along a proper focal distance 32.

Lens 29 is preferably anti-reflection coated, to improve upon a total transmission of only 92% characteristic for uncoated lenses, and to reduce hazards caused, for example, by reflections traveling backwards through the system (ghost images). A ¼λ thick Magnesium Fluoride broadband coating (400–750 nm typical) is preferably used for substrates with an index of refraction ranging from 1.45 to 2.40. This coating is less sensitive to angular and spectral variations than multi-layer dielectric coatings. The performance of the coating will increase as the index of refraction of the substrate increases.

Each lens unit 27, 29 is fixedly positioned and aligned in one of a plurality of cavities 59 in housing 58, using conventional means. Each cavity 59 is in communication with recess 60, so that, when carrier 57 is positioned adjacent to recess 60, each of the plurality of LEDs 22 are received in an appropriated position in relation to a lens 27. Each of a plurality of bores 61 is in communication with a cavity 59 at an opposing end of the cavity 59 in order to fixedly receive an input end 62 of fiber optic assembly 26, so that each input surface 33 of the fiber optic assembly 26 is positioned at a proper focal length 32 and orientation with respect to an associated lens unit 27, 29.

Chamber 38 of housing 58 provides a space for orienting fiber optic assembly 26 so that an output end 63 of fiber optic assembly 26 can be fixedly positioned at an opposing end of chamber 38. Transmitting surface 34 of fiber optic assembly 26 is thereby effectively positioned with respect to input-surface 35 of light guide 37 in order to facilitate transmittance of light energy from fiber optic assembly 26 to light guide 37. Output end 63 of fiber optic assembly 26 may be fixedly positioned in chamber 38 by a variety of conventional means such as, for example, insert 64 which interferingly rests at a desired position in chamber 38. Light guide 37 is fixedly mounted in forward recess 65 of housing 58, having for example a conventional geometry and employing conventional means for fixedly mounting light guide 37 to housing 58.

Figure 9:
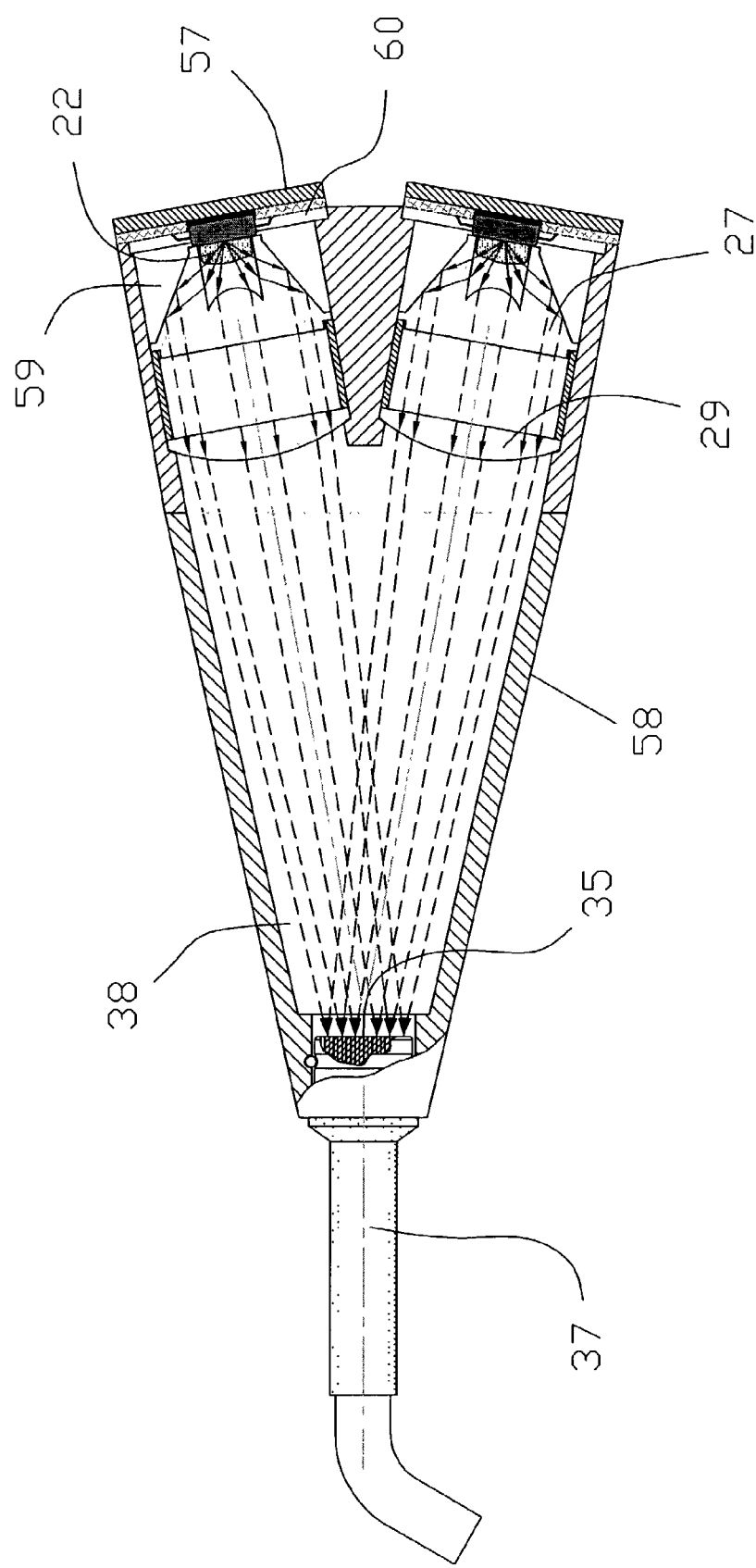

FIG. 9 illustrates an alternate embodiment to the inventive apparatus illustrated in FIGS. 8a, b. In FIG. 9, each LED 22 is mounted is mounted on one of a plurality of carriers 57, each carrier 57 being installed abutting one of a plurality of rearward recesses 60 in light housing 58. Each recess 60 communicates with a cavity 59, and each cavity 59 fixedly holds a lens unit 27, 29 for focusing and condensing light emitted by the LED 22 on input surface 35 of light guide 37. Cavities 59 communicate with chamber 38 so that light transmitted via lens unit 27, 29 travels directly through cavity 38 to input surface 35 without a need, for example, to be directed by the fiber optic assembly 26 of FIGS. 8a, b.

Figure 10:
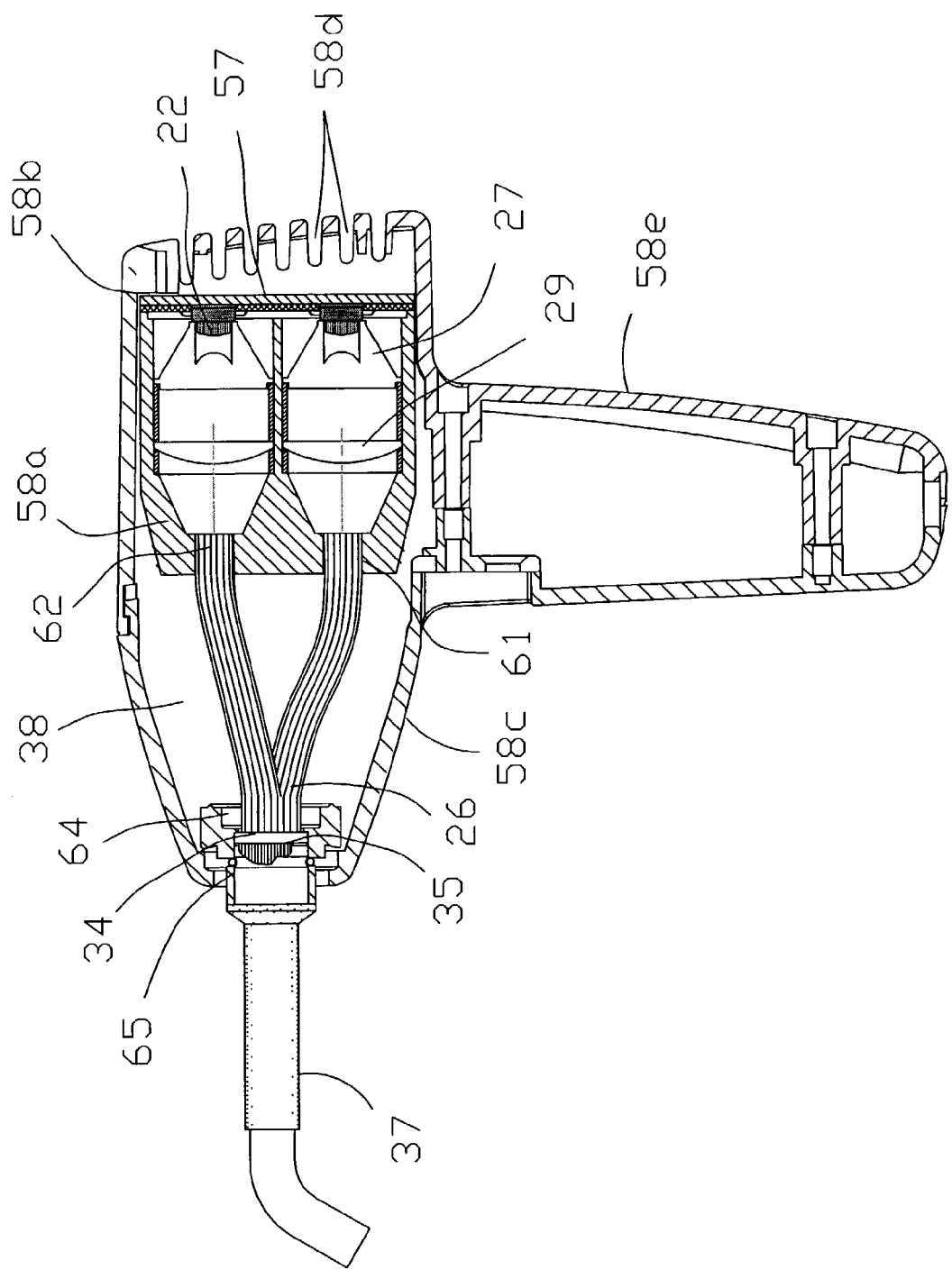
FIG. 10 illustrated a dental curing light that incorporates the inventive apparatus of FIGS. 6a, 6b, 8a, and 8b.

FIG. 10 illustrates the embodiment of FIG. 8a, b packaged for use, for example, in a dental curing light. In FIG. 10, housing 58a houses lens units 27, 29 and carrier 57, which mounts LEDs 22. Housing 58a also contains bores 61 for locating input ends 62 of fiber optic assembly 26 in their desired position relative to lens units 27, 29. Carrier 57, after assembly in housing 58a, is positioned against locating surface 58b in order to locate the assembly 58a, 57 within chamber 38 of exterior housing 58c. At a forward end of exterior housing 58c, transmitting surface 34 of fiber optic assembly 26 is held in a desired position with respect to input surface 35 of light guide 37 by retainer 64. Exterior housing 58c includes a handle portion 58e for convenient gripping and accommodation of a trigger (not shown) for operating the curing light. Housing 58c also includes slots 58d in proximity to carrier 57 to assist in dissipating heat generated by carrier 57. For clarity in illustrating the present invention, other conventional elements of the curing light that may be located, for example, within the handle portion 58e, are not shown in FIG. 9.

The foregoing describes the invention in terms of embodiments foreseen by the inventor for which an enabling description was available, notwithstanding that insubstantial modifications of the invention, not presently foreseen, may nonetheless represent equivalents thereto.

We claim:

1. A light for a curing instrument, comprising:
    first and second light sources, wherein each of the first and second light sources includes a collimator element and a corresponding plano-convex element for producing an incident light beam; and
    means for integrating each of the incident light beams into an output light beam, said integrating means including an least one of a chamber, a fiber optic assembly and a light guide for outputting said output light beam;
    wherein the first one of the light sources has a first characteristic wavelength and the second one of the light sources has a second characteristic wavelength, and the output light beam exhibits an intensity that varies by no more than 25 percent over a range defined between the first and second characteristic wavelengths, selected such that the curing instrument is effective for curing at all wavelengths between at least said first and second characteristic wavelengths.

2. The light of claim 1, wherein the first and second light sources are light emitting diodes (LEDs).

3. The light of claim 1, wherein the range defined by the first and second characteristic wavelengths is about 32 nanometers (nm).

4. The light of claim 3, wherein the first characteristic wavelength is about 460 nm.

5. The light of claim 1, wherein the output light beam has a spectral width of about 69 nm.

6. The light of claim 1, wherein the intensity of the output light beam over a range defined by the first and second characteristic wavelengths is no less than 90 percent of a maximum intensity among the incident light beams produced by the first and second light sources.

7. A method for producing a light for a curing instrument, comprising the steps of:
    providing first and second light sources, wherein each of the first and second light sources includes a collimator element and a corresponding plano-convex element for producing an incident light beam; and
    integrating each of the incident light beams into an output light beam, said integrating step being performed through at least one of a chamber, a fiber optic assembly, and light guide;
    wherein the first light source has a first characteristic wavelength and a first spectral width ending at an uppermost wavelength, the second light source has a second characteristic wavelength and a second spectral width beginning at a lowermost wavelength, and the first and second light sources are selected such that the uppermost wavelength of the first light source and the lowermost wavelength of the second light source are approximately coincident, and such that the output light beam is effective for curing a all wavelengths between said first and second characteristic wavelengths.

* * * * *